United States Patent
Yoon et al.

(10) Patent No.: US 10,941,172 B2
(45) Date of Patent: Mar. 9, 2021

(54) CHEMICAL METHOD FOR PREPARING HEME IRON NOT DERIVED FROM PORCINE BLOOD

(71) Applicant: INTRON BIOTECHNOLOGY, INC., Gyeonggi-do (KR)

(72) Inventors: Seong Jun Yoon, Seoul (KR); Jung In Pyo, Seoul (KR); Soon Hye Hwang, Gyeonggi-do (KR); Soo Youn Jun, Seoul (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 0 days.

(21) Appl. No.: 16/475,410

(22) PCT Filed: Dec. 6, 2017

(86) PCT No.: PCT/KR2017/014174
§ 371 (c)(1),
(2) Date: Jul. 2, 2019

(87) PCT Pub. No.: WO2018/128281
PCT Pub. Date: Jul. 12, 2018

(65) Prior Publication Data
US 2019/0345182 A1     Nov. 14, 2019

(30) Foreign Application Priority Data

Jan. 3, 2017  (KR) .......................... 10-2017-0000520

(51) Int. Cl.
*C07D 487/22* (2006.01)
*C07F 15/02* (2006.01)
*A61K 31/555* (2006.01)

(52) U.S. Cl.
CPC .......... *C07F 15/025* (2013.01); *A61K 31/555* (2013.01); *C07D 487/22* (2013.01)

(58) Field of Classification Search
CPC .................................................. C07D 487/22
See application file for complete search history.

(56) References Cited

U.S. PATENT DOCUMENTS

| | | |
|---|---|---|
| 4,431,581 A | 2/1984 | Lindroos |
| 5,008,388 A | 4/1991 | Inberg et al. |
| 6,420,553 B1 | 7/2002 | Inoue et al. |
| 6,479,477 B1 | 11/2002 | Crapo et al. |
| 8,026,358 B2 | 9/2011 | Martin et al. |
| 8,420,805 B2 | 4/2013 | Martin et al. |
| 9,334,513 B2 | 5/2016 | Kim |
| 2008/0242857 A1 | 10/2008 | Martin et al. |
| 2011/0213142 A1 | 9/2011 | Kim |
| 2011/0306761 A1 | 12/2011 | Martin et al. |

FOREIGN PATENT DOCUMENTS

| | | |
|---|---|---|
| JP | H11255790 A | 9/1999 |
| KR | 1020090127139 A | 12/2009 |
| KR | 1020110070977 A | 6/2011 |
| KR | 101431453 B1 | 8/2014 |
| WO | WO 2018/128281 A1 | 7/2018 |

OTHER PUBLICATIONS

Liu, et. al.,"Physicochemical Properties of Aggregates of Globin Hydrolysates" J. Agric. Food Chem.1996,44(10):2957-2961.
International Search Report dated Mar. 20, 2018 by the International Searching Authority for International Application No. PCT/KR2017/014174, filed on Dec. 6, 2017 and published as WO 2018/128281 on Jul. 12, 2018 (Applicant—Intron Biotechnology, Inc.) (Translation—3 Pages).

*Primary Examiner* — Brian E McDowell
(74) *Attorney, Agent, or Firm* — Ballard Spahr LLP

(57) ABSTRACT

Described is heme iron having Chemical Formula 1 not derived from porcine blood and a method of preparing the same, and more particularly to a method of chemically preparing heme iron having Chemical Formula 1 not derived from porcine blood, a method of preparing a salt thereof, and an iron supplement containing the salt thus prepared as an active ingredient:

[Chemical Formula 1]

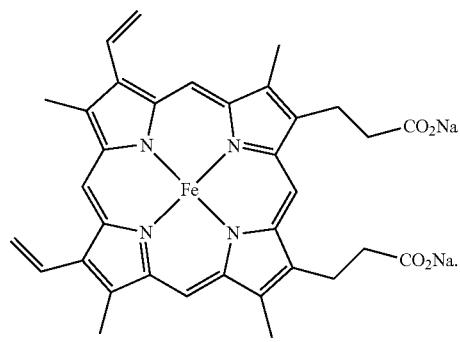

8 Claims, 4 Drawing Sheets

[FIG. 1]
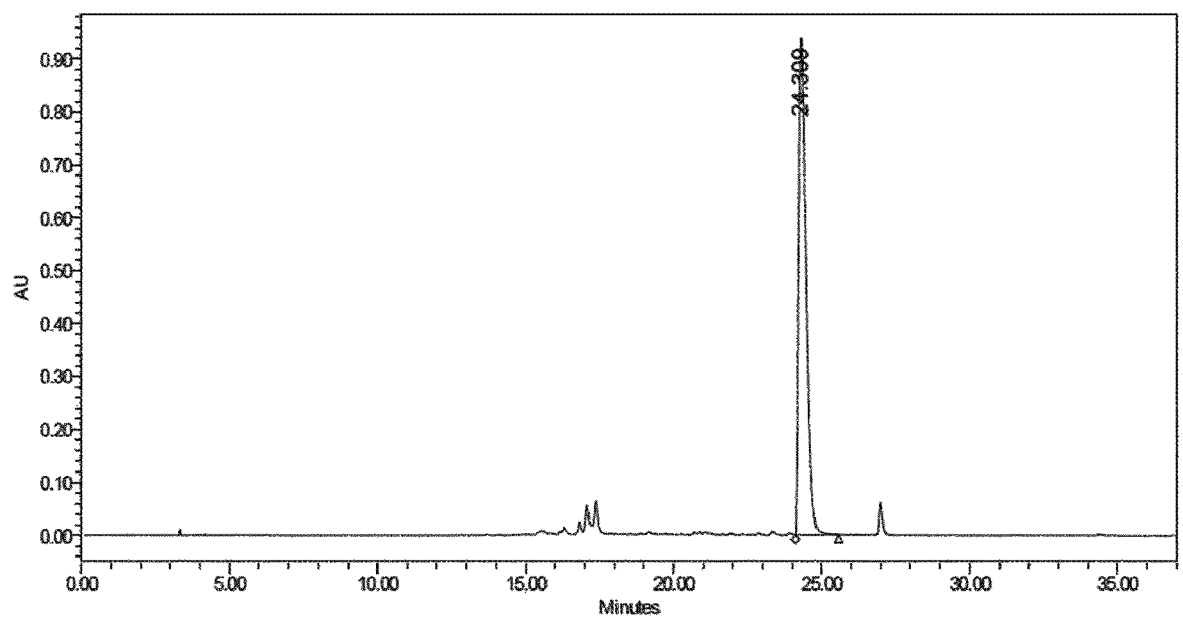

[FIG. 2]
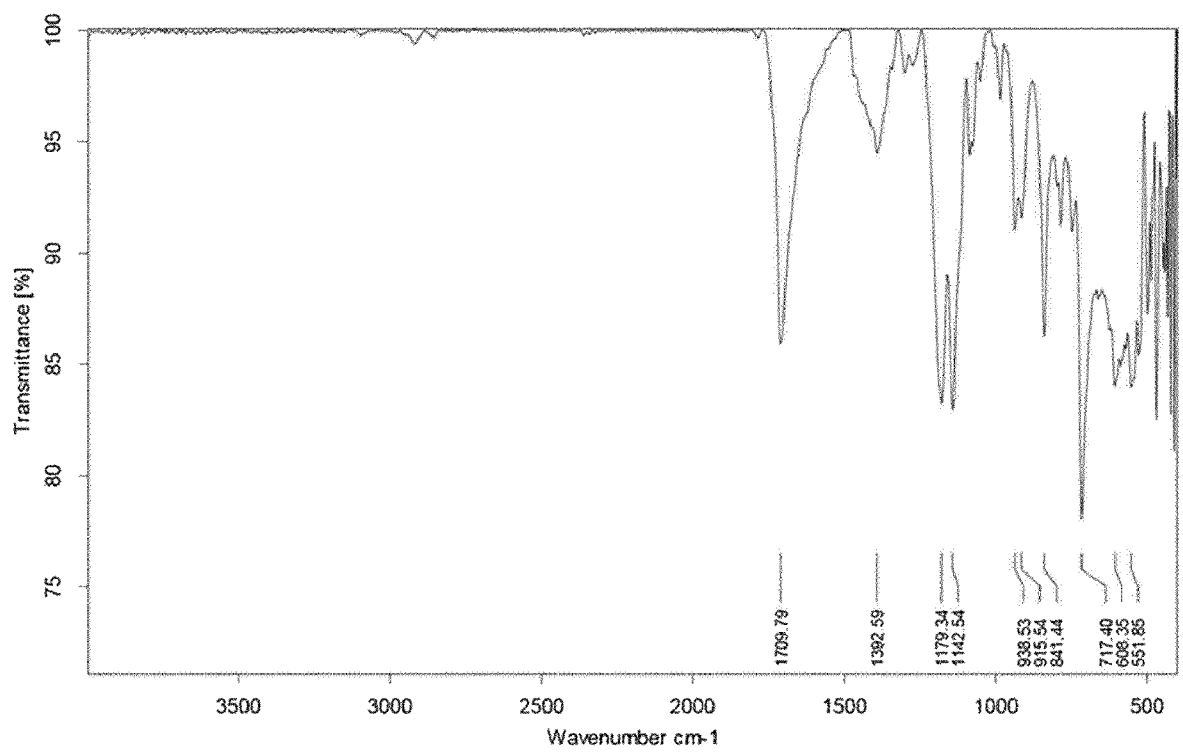

[FIG. 3]
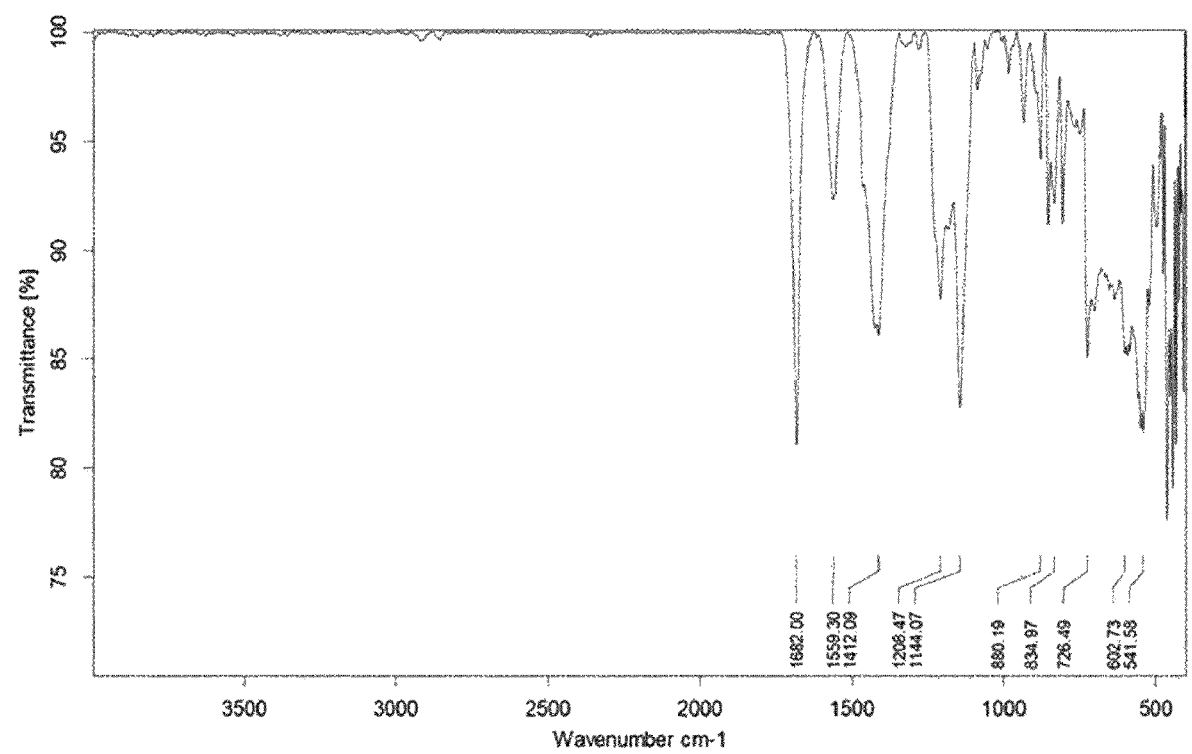

[FIG. 4]
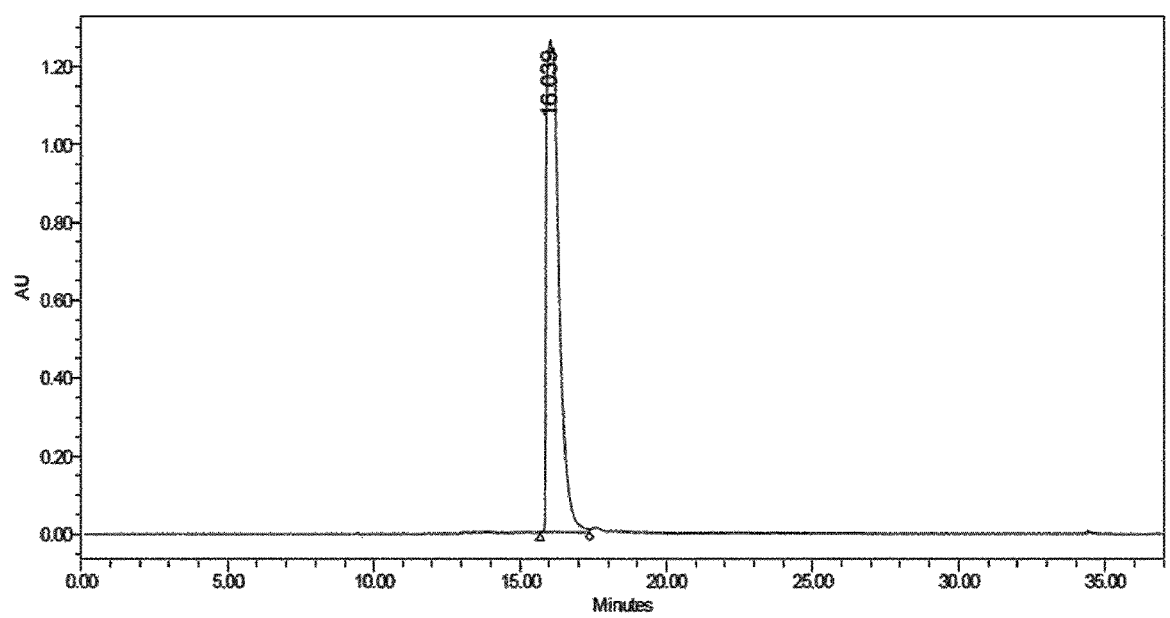

CHEMICAL METHOD FOR PREPARING HEME IRON NOT DERIVED FROM PORCINE BLOOD

CROSS-REFERENCE TO RELATED APPLICATIONS

This application is a U.S. National Phase Application of International Application No. PCT/KR2017/014174, filed Dec. 6, 2017, which claims priority to Korean Application No. 10-2017-0000520, filed Jan. 3, 2017, each of which are hereby incorporated by reference in their entirety.

TECHNICAL FIELD

The present invention relates to heme iron containing no animal-derived component and a method of preparing the same, and more particularly to a method of chemically preparing heme iron not derived from porcine blood, which is characterized in containing no animal-derived component, a method of preparing a salt thereof, and an iron supplement containing the salt thus prepared as an active ingredient.

BACKGROUND ART

Iron (Fe) is a trace element that plays an essential role for oxygen transport in the body, and is an important constituent of hemoglobin, myoglobin, cytochrome, iron/sulfur protein and biomolecular structures. The total amount of iron in the body is about 3 to 4 g, 60 to 65% of which is bound to hemoglobin in circulating erythrocytes, and the remaining 30 to 35% is present as storage iron (ferritin). Iron is also present in the form of tissue iron and serum iron (transferrin), and furthermore, there is a small amount of iron in myoglobin of the muscles.

Iron is not synthesized in the body and thus must be acquired entirely through intake, and exists in two types, heme iron and nonheme iron. Heme iron is an iron complex having a moiety having the same structure as the heme of hemoglobin in the body, and nonheme iron is an iron complex not having a moiety having the same structure as the heme of hemoglobin. These two may be used as iron supplements (iron supplementary compound), and the bioavailability of heme iron is known to be much higher than that of nonheme iron. Also, the absorption of heme iron in the body is not affected by other dietary factors. Moreover, heme iron has the advantage of not causing various side effects (constipation, gastrointestinal disorders, etc.) that have been reported for nonheme iron.

Generally, heme iron is manufactured from blood of slaughtered animal, such as porcine blood. The heme iron is prepared from slaughterhouse blood by a manner in which hemoglobin is first separated from the slaughterhouse blood and then heme iron is isolated from the separated hemoglobin. The separation of heme iron from hemoglobin may be performed through a method of using an alcohol and an imidazole derivative (Lindroos, U.S. Pat. No. 4,431,581), a method of adding amino acids thereto (Ingberg, et. al., U.S. Pat. No. 5,008,388), a method of performing decomposition at a high temperature using a highly concentrated organic acid (Liu, et. al., *J. Agric. Food Chem.*, 44, 2957, 1996), a method of using a protease, and the like.

Heme iron thus prepared has many problems that are not present in nonheme iron, such as the risk of infection by animal-derived infection sources, livestock growth hormone contamination, and residual antibiotics. Moreover, the preparation of heme iron as described above involves the production of heme iron from blood obtained from the slaughter of animals such as pigs, which is forbidden by Islam, and thus the heme iron above prepared does not conform to halal regulations, undesirably obstructing the use thereof as an iron supplement by Muslims.

Therefore, it is necessary to develop a method of preparing heme iron not derived from porcine blood.

DISCLOSURE

Technical Problem

Accordingly, the present invention has been made keeping in mind the problems encountered in the related art and is intended to solve such problems.

An objective of the present invention is to provide a process of chemically preparing heme iron that is not derived from porcine blood.

Another objective of the present invention is to provide a method of preparing a salt of the heme iron obtained through the process of chemically preparing heme iron not derived from porcine blood.

Still another objective of the present invention is to provide a pharmaceutical composition for the prevention of iron-deficiency anemia, containing the salt of the heme iron obtained through the process of chemically preparing heme iron not derived from porcine blood, as a main ingredient, without containing any animal component.

Yet another objective of the present invention is to provide a pharmaceutical composition for the treatment of iron-deficiency anemia, containing the salt of the heme iron obtained through the process of chemically preparing heme iron not derived from porcine blood, as a main ingredient, without containing any animal component.

Technical Solution

In order to accomplish the above objectives, the present inventors have, as the result of intensive study, developed a process of chemically preparing heme iron not derived from porcine blood, a method of preparing a salt of the heme iron above prepared, and a pharmaceutical composition containing no animal component using the salt of the heme iron above prepared, and have ascertained that the composition may be effectively utilized for the treatment of iron-deficiency anemia, thus culminating in the present invention.

According to the present invention, the salt of heme iron is a material having the structure of Chemical Formula 1 below.

[Chemical Formula 1]

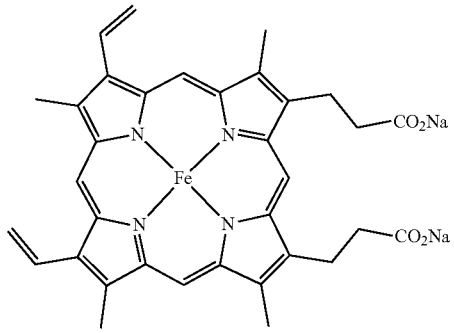

The above process of chemically preparing heme iron without using porcine blood is a reaction process for the coordination of iron to protoporphyrin or a reaction process for the coordination of iron to protoporphyrin dimethyl ester.

The above reaction process for the coordination of iron to protoporphyrin is represented in Scheme 1 below.

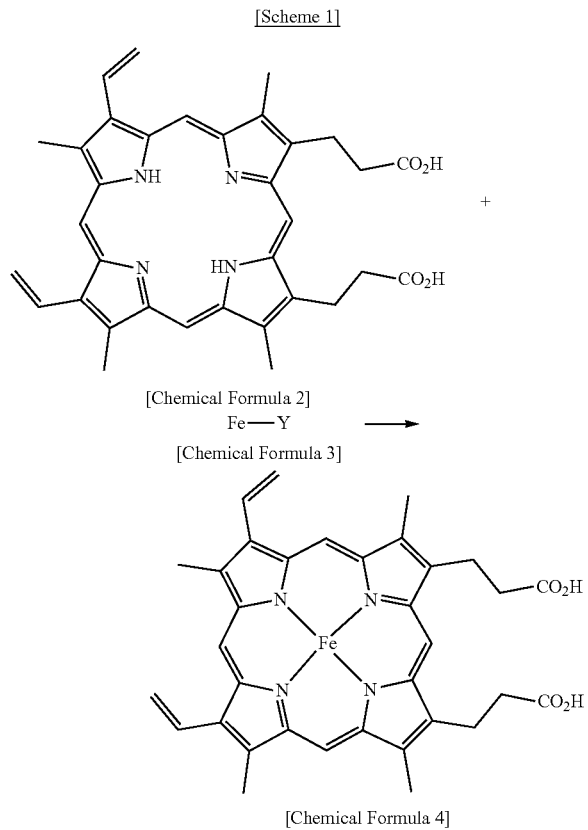

[Scheme 1]

[Chemical Formula 2]
Fe—Y

[Chemical Formula 3]

[Chemical Formula 4]

With regard to the above reaction process for the coordination of iron to protoporphyrin, the reaction for the coordination of a metal element to a porphyrin compound is typically carried out through heating at a high temperature of 100° C. or more for a long period of time or by applying microwaves at a high temperature of 100° C. or more, but the present inventors have searched for optimal solvent conditions and temperature ranges and applied these conditions to the preparation of heme iron, thereby making it possible to prepare heme iron through the coordination of iron to protoporphyrin under milder conditions.

As the solvent for the above reaction process for the coordination of iron to protoporphyrin, any organic solvent that is typically useful in the art may be used, and examples thereof may include 1,2-dichloroethane, N,N-dimethylformamide, 1,4-dioxane, tetrahydrofuran, methyltetrahydrofuran, dimethyltetrahydrofuran, and the like. However, in the reaction for the coordination of iron to protoporphyrin, the use of N,N-dimethylformamide or tetrahydrofuran may result in the greatest reaction efficiency.

The above reaction process for the coordination of iron to protoporphyrin is preferably carried out at a temperature of 55 to 100° C., and more preferably 60 to 70° C.

The iron compound, which may be used in the above reaction process for the coordination of iron to protoporphyrin, may be selected from the group consisting of $FeCl_2 \cdot 4H_2O$, $FeBr_2 \cdot 4H_2O$ and $FeI_2 \cdot 4H_2O$, and the use of $FeCl_2 \cdot 4H_2O$ is most preferable. In the above reaction process for the coordination of iron to protoporphyrin, the iron compound is preferably used in an amount of 2 to 5 equivalents based on the equivalents of protoporphyrin.

In order to remove unreacted iron ions, which are left behind after the above reaction for the coordination of iron to protoporphyrin, ion exchange resin column chromatography, silica gel column chromatography, or diatomaceous earth column chromatography, which are typically useful in the art, may be performed.

With regard to the above reaction process for the coordination of iron to protoporphyrin dimethyl ester, the reaction for the coordination of a metal element to a porphyrin compound is typically carried out through heating at a high temperature of 100° C. or more for a long period of time or by applying microwaves at a high temperature of 100° C. or more, but the present inventors have searched for optimal solvent conditions and temperature ranges and applied these conditions to the preparation of heme iron, thereby making it possible to prepare heme iron through the coordination of iron to protoporphyrin dimethyl ester under milder conditions.

As the solvent for the above reaction process for the coordination of iron to protoporphyrin dimethyl ester, any organic solvent that is typically useful in the art may be used, and examples thereof may include 1,2-dichloroethane, N,N-dimethylformamide, 1,4-dioxane, tetrahydrofuran, methyltetrahydrofuran, dimethyltetrahydrofuran, and the like. However, the use of N,N-dimethylformamide or tetrahydrofuran is most efficient.

The above reaction process for the coordination of iron to protoporphyrin dimethyl ester is preferably carried out at a temperature of 55 to 100° C., and more preferably 60 to 70° C.

The iron compound useful in the above reaction process for the coordination of iron to protoporphyrin dimethyl ester may be selected from the group consisting of $FeCl_2 \cdot 4H_2O$, $FeBr_2 \cdot 4H_2O$ and $FeI_2 \cdot 4H_2O$, the use of $FeCl_2 \cdot 4H_2O$ being most preferable. In the above reaction process for the coordination of iron to protoporphyrin dimethyl ester, the iron compound is preferably used in an amount of 2 to 5 equivalents based on the equivalents of protoporphyrin dimethyl ester.

In order to remove unreacted iron ions, which are left behind after the above reaction for the coordination of iron to protoporphyrin dimethyl ester, ion exchange resin column chromatography, silica gel column chromatography, or diatomaceous earth column chromatography, which are typically useful in the art, may be performed.

In the method of preparing the salt of the heme iron obtained through the above process of chemically preparing heme iron not derived from porcine blood, the chlorination reaction for preparing a salt in the case of coordination of iron to protoporphyrin may be carried out at room temperature through the addition of a NaOH aqueous solution or a KOH aqueous solution. Here, the use of a NaOH aqueous solution is more preferable. The chlorination reaction for preparing a salt in the case of coordination of iron to protoporphyrin dimethyl ester may be carried out under reflux conditions through the addition of a NaOH aqueous solution or a KOH aqueous solution. Here, the use of a NaOH aqueous solution is more preferable.

According to the present invention, the process of preparing heme iron is capable of realizing the preparation of heme iron from a pure single material, making it possible to produce high-purity heme iron without the need for an excessive purification process. Generally, heme iron having a purity of 95% or more and a salt thereof may be prepared, and as necessary, the process of preparing heme iron according to the present invention may be applied to the preparation of heme iron having a purity of 99% or more and a salt thereof.

As used herein, the term "heme iron" refers to an iron complex comprising a moiety having the same structure as the heme of hemoglobin in the body, and the term "nonheme iron" refers to an iron complex not comprising a moiety having the same structure as the heme of hemoglobin.

A pharmaceutically acceptable carrier, which is contained in the composition of the present invention, may be any example thereof typically useful for formulation, and may include, but is not limited to, lactose, dextrose, sucrose, sorbitol, mannitol, starch, acacia rubber, calcium phosphate, alginate, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil and the like. The composition of the present invention may further contain, in addition to the above components, a lubricant, a wetting agent, a sweetener, a flavoring agent, an emulsifier, a suspending agent, a preservative, and the like.

The composition of the present invention may be formulated using a pharmaceutically acceptable carrier and/or excipient in accordance with a method that may be easily carried out by those skilled in the art to which the present invention belongs, and be prepared in a unit dosage form or insert the same into a multi-dose container. Here, the formulation thereof may be provided in the form of a solution in an oil or aqueous medium, a suspension or an emulsion, or in the form of an extract, a powder, a granule, a tablet, or a capsule, and may additionally contain a dispersant or a stabilizer.

Advantageous Effects

According to the present invention, a process of chemically preparing heme iron not derived from porcine blood can be provided. The heme iron thus prepared can provide various characteristic advantages of heme iron compared to nonheme iron, and can also overcome many problems related with existing heme iron made from porcine blood. In particular, since the use of porcine blood is fundamentally excluded, the heme iron thus prepared can also be utilized in the production of halal iron supplements. Moreover, the process of preparing heme iron according to the present invention is advantageous because heme iron can be prepared from a pure single material, thus enabling the preparation of high-purity heme iron.

DESCRIPTION OF DRAWINGS

FIG. 1 shows a chromatogram of HPLC (high-performance liquid chromatography) of protoporphyrin;

FIG. 2 shows the analysis results of FT-IR (Fourier transform infrared spectroscopy) for the material of Chemical Formula 4, prepared according to the present invention;

FIG. 3 shows the analysis results of FT-IR for the material of Chemical Formula 1, prepared according to the present invention; and FIG. 4 shows a chromatogram of HPLC of the material of Chemical Formula 4, prepared according to the present invention.

MODE FOR INVENTION

Hereinafter, a better understanding of the present invention will be given through the following examples, which are merely set forth to illustrate the present invention but are not to be construed as limiting the scope of the present invention.

Example 1

Preparation of Heme Iron Using Protoporphyrin

[Scheme 2]

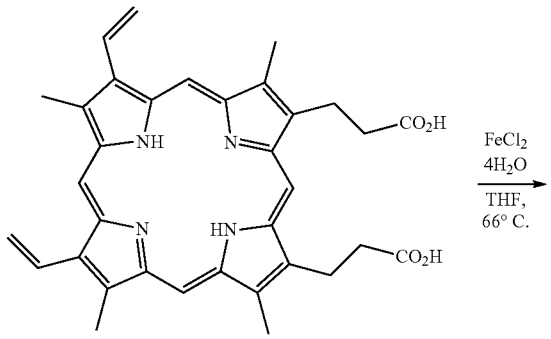

[Chemical Formula 2]

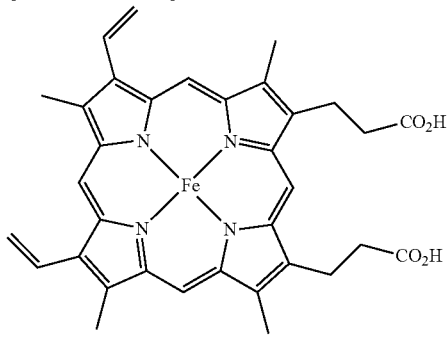

[Chemical Formula 4]

Chemical Formula 2 (10 g, 17.8 mmol) was dissolved in tetrahydrofuran (150 ml), slowly added with $FeCl_2 \cdot 4H_2O$ (14.4 g, 53.3 mmol), and heated at 66° C. for 3 hr. After termination of the reaction, the organic solvent was removed through vacuum distillation. Next, the reaction mixture was added with a NaOH aqueous solution and was thus dissolved therein, the resulting solution was filtered through a column packed with Celite® 545, and the filtrate thus obtained was neutralized, thereby yielding Chemical Formula 4 (10.8 g, 99%).

IR: 1709, 1392, 1179, 1142, 938, 915, 841, 717, 608, 551 $cm^{-1}$; MS (ESI) Calcd for $C_{34}H_{32}FeN_4O_4$: 616.2, found: m/z 616.2; UV-vis (DMSO, nm) $\lambda_{max}$ 348, 386; ICP-OES Calcd for Fe: 9.06%, found: 9.0%.

Example 2

Chlorination Reaction of Heme Iron Prepared Using Protoporphyrin

A solution of NaOH (630 mg, 15.9 mmol) dissolved in distilled water (15 ml) was added with Chemical Formula 4 (5 g, 8.11 mmol) obtained in Example 1 and subjected to chlorination reaction with stirring at room temperature for 30 min. After termination of the reaction, the reaction mixture was frozen at 80° C. and then freeze-dried and thus dewatered, thereby yielding Chemical Formula 1 (5.25 g, 98%).

IR: 1682, 1559, 1412, 1208, 1144, 880, 834, 726, 602, 541 cm$^{-1}$; MS (ESI) Calcd for $C_{34}H_{30}FeN_4Na_2O_4$: 660.1, found: m/z 660.2.

Example 3

Preparation Method of Heme Iron and Salt Thereof Using Protoporphyrin Dimethyl Ester Protoporphyrin dimethyl ester (5 g, 8.5 mmol) was dissolved in tetrahydrofuran (150 ml), slowly added with $FeCl_2 \cdot 4H_2O$ (5.04 g, 25.3 mmol) and heated at 66° C. for 3 hr. After termination of the reaction, the organic solvent was removed through vacuum distillation. Next, the reaction mixture was added with a NaOH aqueous solution and thus dissolved therein, the resulting solution was filtered through a column packed with Celite® 545, and the solution thus obtained was neutralized and freeze-dried (crude yield: 95%). The freeze-dried compound was dissolved in a NaOH aqueous solution of NaOH (700 mg, 17.7 mmol) dissolved in distilled water (15 ml) and then subjected to chlorination reaction with stirring under reflux for 30 min. After termination of the reaction, the reaction mixture was frozen at 80° C. and then freeze-dried and thus dewatered, thereby yielding Chemical Formula 1 (4.46 g, 90%).

IR: 1682, 1559, 1412, 1208, 1144, 880, 834, 726, 602, 541 cm$^{-1}$; MS (ESI) Calcd for $C_{34}H_{30}FeN_4Na_2O_4$: 660.1, found: m/z 660.2.

Example 4

Identification of Prepared Heme Iron

In order to identify the prepared heme iron and the salt thereof, various analyses were performed. Specifically, FT-IR, mass spectrometry, UV-vis spectrophotometry, and ICP-OES were conducted. The analysis results of heme iron are summarized below. These results were consistent with expectations. For reference, the results of FT-IR are shown in FIG. 2.

TABLE 1

Analysis results of heme iron

| Analysis method | Analysis results |
|---|---|
| FT-IR | 1709, 1392, 1179, 1142, 938, 915, 841, 717, 608, 551 cm$^{-1}$ |
| Mass spectrometry | (ESI) Calcd for $C_{34}H_{32}FeN_4O_4$: 616.2, found: m/z 616.2 |
| UV-vis spectrophotometry | (DMSO, nm) $\lambda_{max}$ 348, 386 |
| ICP-OES | Calcd for Fe: 9.06%, found: 9.0% |

Meanwhile, the analysis results for the salt of heme iron are summarized below. These results were consistent with expectations. For reference, the results of FT-IR of the salt of heme iron are shown in FIG. 3.

TABLE 2

Analysis results for salt of heme iron

| Analysis method | Analysis results |
|---|---|
| FT-IR | 1682, 1559, 1412, 1208, 1144, 880, 834, 726, 602, 541 cm$^{-1}$ |
| Mass spectrometry | (ESI) Calcd for $C_{34}H_{30}FeN_4Na_2O_4$: 660.1, found: m/z 660.2 |

The purity of heme iron prepared according to the present invention was measured through HPLC. The results thereof are shown in FIG. 4. As is apparent from the results of FIG. 4, high-purity heme iron can be prepared according to the preparation process of the present invention. This is because the preparation process of the present invention makes it possible to prepare heme iron from a pure single material. Generally, heme iron having a purity of 95% or more may be prepared, without the need for excessive purification, and the preparation of heme iron having a purity of 99% or more is also possible.

Example 5

Evaluation for Effectiveness of Heme Iron as Iron Supplementary Source

The salt of the heme iron prepared according to the present invention was dissolved in saline and administered to iron-deficiency-anemia-induced animals, whereby the effectiveness of the salt of the heme iron prepared according to the present invention on alleviating anemia was evaluated.

Specifically, forty 7-week-old Sprague-Dawley rats (female) were divided into 4 groups of 10 rats per group, among which one group was fed with normal feed in an amount of 10% of body weight daily for one month (Group 1; control), and the remaining three groups were fed with iron-deficient feed in an amount of 10% of body weight daily for one month to induce iron-deficiency anemia (Group 2, Group 3, and Group 4). After one month of feeding, it was confirmed that iron-deficiency anemia was induced in the individual rat belonging to Group 2, Group 3, and Group 4. Then, one of the anemia-induced groups was orally administered once a day with saline alone (Group 2), another anemia-induced group was orally administered once a day with saline containing the salt of heme iron prepared in Example 2 (0.1 mg Fe/500 μl saline) (Group 3), and the other anemia-induced group was orally administered once a day with saline containing the salt of heme iron prepared in Example 3 (0.1 mg Fe/500 μl saline) (Group 4). The administration continued for 30 days, and the occurrence of abnormal symptoms was monitored during the administration period. After 30 days of administration, blood was collected, and whether the anemia was alleviated was evaluated. During 30 days of administration to Group 2, Group 3, and Group 4, Group 1 was continuously fed with normal feed. Group 2, Group 3, and Group 4 were fed with iron-deficient feed. There were no abnormal symptoms in any animals during the 30 days of administration period. The analysis results of blood collection are shown below.

TABLE 3

Analysis results of blood collection

| Group No. | Treatment | Weight of rats on 30$^{th}$ day after administration [g] | Blood test | | |
|---|---|---|---|---|---|
| | | | Hemoglobin content [g/dl] | RBC [×10$^6$/μl] | Mean corpuscular volume [fl] | Hematocrit [%] |
| Group 1 | Normal feed | 274.5 ± 2.7 | 14.4 ± 0.7 | 8.60 ± 0.3 | 47.0 ± 1.4 | 36.2 ± 2.4 |
| Group 2 | Iron-deficient feed + saline | 278.2 ± 2.5 | 10.8 ± 0.9 | 8.74 ± 0.4 | 34.9 ± 3.4 | 34.2 ± 2.2 |
| Group 3 | Iron-deficient feed + heme iron 1 | 266.2 ± 1.6 | 14.4 ± 0.8 | 8.61 ± 0.4 | 47.9 ± 2.5 | 36.4 ± 1.7 |
| Group 4 | Iron-deficient feed + heme iron 2 | 265.4 ± 1.4 | 14.3 ± 0.6 | 8.59 ± 0.5 | 46.9 ± 2.6 | 35.8 ± 1.6 |

As is apparent from the above results, the heme iron of the present invention can be concluded to be effective at alleviating iron-deficiency anemia and is thus efficient material as an iron supplementary source. Also, the heme iron of the present invention and the salt thereof can be confirmed to be useful not only in the treatment of iron-deficiency anemia but also in the prevention thereof.

Reference Examples

These Reference Examples were performed in order to determine the optimal reaction conditions for carrying out an iron coordination reaction using protoporphyrin.

Reference Example 1

Comparison for Importance of Iron Ion Selection in Iron Coordination

Chemical Formula 4 was obtained through the coordination of iron in the same manner as in above Example 1, with the exception that the iron ions shown in Table 4 below were used. The results of coordination of individual iron ions in the same manner as in Example 1 are shown in Table 4 below.

TABLE 4

Effects of iron supplementary source

| No. | Iron ion | Solvent | Reaction time | Yield |
|---|---|---|---|---|
| 1 | Fe(OAC)$_2$ | Tetrahydrofuran | 5 hr | −$^c$ |
| 2 | FeCl$_2$ | | 24 hr | ++$^b$ |
| 3 | FeCl$_2$·4H$_2$O | | 3 hr | ++++$^a$ |
| 4 | (NH$_4$)$_2$FeSO$_4$·6H$_2$O | | 5 hr | −$^c$ |

+ (0~25%);
++ (26~50%);
+++ (51~80%);
++++ (81~99%)
$^a$Isolated yield;
$^b$HPLC observed value;
$^c$No product Table 4 shows the coordination reactions using various iron ions. The use of FeCl$_2$·4H$_2$O resulted in completion of the coordination at a high yield within a short time.

Reference Example 2

Comparison for Importance of Solvent Selection in Iron Coordination

Chemical Formula 4 was obtained through the coordination of iron in the same manner as in above Example 1, with the exception that the solvents shown in Table 5 below were used. The results thereof are shown below.

TABLE 5

Effects of solvent

| No. | Solvent | Iron ion | Reaction time | Yield |
|---|---|---|---|---|
| 1 | Ethyl acetate | FeCl$_2$·4H$_2$O | 15 hr | −$^c$ |
| 2 | Butyl acetate | | 10 hr | +$^b$ |
| 3 | Methylene chloride | | 15 hr | −$^c$ |
| 4 | Acetonitrile | | 12 hr | +$^b$ |
| 5 | Acetone | | 10 hr | −$^c$ |
| 6 | Methyl ethyl ketone | | 8 hr | +$^b$ |
| 7 | 1,2-dichloroethane | | 5 hr | +$^b$ |
| 8 | 1,4-dioxane | | 3.5 hr | ++$^b$ |
| 9 | N,N-dimethylformamide | | 2.5 hr | ++++$^b$ |
| 10 | Tetrahydrofuran | | 3 hr | ++++$^a$ |
| 11 | Toluene | | 5 hr | +$^b$ |

+ (0~25%);
++ (26~50%);
+++ (51~80%);
++++ (81~99%)
$^a$Isolated yield;
$^b$HPLC observed value;
$^c$No product As is apparent from above Table 5, the use of N,N-dimethylformamide or tetrahydrofuran resulted in completion of the iron coordination at a high reaction rate and a high yield.

Reference Example 3

Preparation Yield of Heme Iron Depending on Reaction Temperature

Chemical Formula 4 was obtained through the coordination of iron in the same manner as in above Example 1, with the exception that the reaction temperatures shown in Table 6 below were applied. The results thereof are shown below.

TABLE 6

Effects of reaction temperature

| No. | Solvent | Iron ion | Reaction time | Reaction temperature | Yield |
|---|---|---|---|---|---|
| 1 | N,N-dimethylformamide | $FeCl_2 \cdot 4H_2O$ | 3 hr | 50~60° C. | +++[b] |
| 2 | | | | 61~70° C. | ++++[a] |
| 3 | | | | 71~80° C. | +++[a] |
| 4 | | | | 81~90° C. | +++[b] |
| 5 | | | | 91~100° C. | ++[b] |
| 6 | | | | 101~110° C. | −[c] |
| 7 | | | | 111~120° C. | −[c] |
| 8 | Tetrahydrofuran | | | 40~50° C. | ++[b] |
| 9 | | | | 50~60° C. | +++[a] |
| 10 | | | | 61~66° C. | ++++[a] |

+ (0~25%);
++ (26~50%);
+++ (51~80%);
++++ (81~99%)
[a]Isolated yield;
[b]HPLC observed value;
[c]No product (unknown)

As is apparent from Table 6, the use of N,N-dimethylformamide (6170° C.) and tetrahydrofuran (6166° C.) resulted in a high yield.

Reference Example 4

Purification Yield of Heme Iron

Chemical Formula 4 was obtained through the coordination of iron in the same manner as in above Example 1, with the exception that the purification was performed under filtration conditions shown in Table 7 below. The results thereof are shown below.

TABLE 7

Effects of filtration material

| No. | Filtration material | Purification time | Purification yield |
|---|---|---|---|
| 1 | Silica gel | 4 hr | ++ |
| 2 | Celite ®545 | 15 min | ++++ |
| 3 | Active carbon | 6 hr | + |
| 4 | Aluminum gel | 3 hr | + |

+ (0~25%);
++ (26~50%);
+++ (51~80%);
++++ (81~99%)

As is apparent from the results of above Table 7, the use of Celite®545 was very favorable for purification.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

The invention claimed is:

1. A method of chemically preparing a salt of heme iron having Chemical Formula 1 below, not derived from porcine blood, containing no animal component, and having high purity, the method comprising:
A) dissolving protoporphyrin IX or protoporphyrin IX dimethyl ester in an organic solvent, adding an iron compound and performing heating;
B) removing the organic solvent; and
C) subjecting a product obtained in step B) to chlorination:

[Chemical Formula 1]

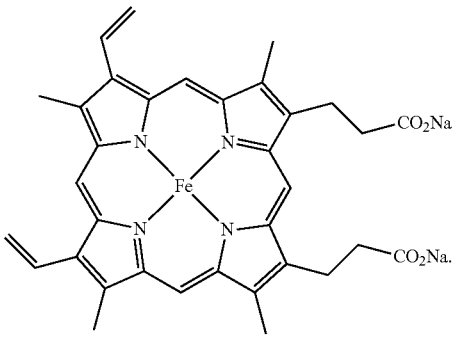

2. The method of claim 1, further comprising a purification process between step B) and step C).

3. The method of claim 1, further comprising a dewatering process after step C).

4. The method of claim 1, wherein step A comprises dissolving protoporphyrin IX in the organic solvent.

5. The method of claim 1, wherein the organic solvent is tetrahydrofuran or N,N-dimethylformamide.

6. The method of claim 1, wherein the iron compound is selected from the group consisting of $FeCl_2 \cdot 4H_2O$, $FeBr_2 \cdot 4H_2O$, and $FeI_2 \cdot 4H_2O$.

7. The method of claim 2, wherein the purification is performed using diatomaceous earth.

8. The method of claim 1, wherein step A comprises dissolving protoporphyrin IX dimethyl ester in the organic solvent.

\* \* \* \* \*